US009770828B2

(12) United States Patent
Taylor et al.

(10) Patent No.: US 9,770,828 B2
(45) Date of Patent: Sep. 26, 2017

(54) TELEOPERATIVE-COOPERATIVE ROBOTIC SYSTEM

(71) Applicant: The Johns Hopkins University, Baltimore, MD (US)

(72) Inventors: Russell H. Taylor, Severna Park, MD (US); Marcin A. Balicki, Baltimore, MD (US); Peter Kazanzides, Baltimore, MD (US); Xia Tian, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 77 days.

(21) Appl. No.: 13/631,035

(22) Filed: Sep. 28, 2012

(65) Prior Publication Data

US 2014/0094968 A1    Apr. 3, 2014

Related U.S. Application Data

(60) Provisional application No. 61/540,145, filed on Sep. 28, 2011.

(51) Int. Cl.
*B25J 13/00* (2006.01)
*B25J 19/04* (2006.01)
(Continued)

(52) U.S. Cl.
CPC .............. *B25J 13/006* (2013.01); *A61B 34/30* (2016.02); *A61B 34/35* (2016.02); *A61B 34/76* (2016.02);
(Continued)

(58) Field of Classification Search
CPC ........ B25J 13/006; B25J 19/04; B25J 9/1633; B25J 13/085; G05B 2219/36429;
(Continued)

(56) References Cited

U.S. PATENT DOCUMENTS 5,116,180 A * 5/1992 Fung et al. ................. 414/5
5,784,542 A * 7/1998 Ohm et al. ................. 700/260
(Continued)

OTHER PUBLICATIONS

EyeSAW-TeleOp2.pdf (Marcin Balicki, Tian Xia, Min Yang Jung, Anton Deguet, Balazs Vagvolgyi, Peter Kazanzides, Russell Taylor, Prototyping a Hybrid Cooperative and Telerobotic Surgical System for Retinal Microsurgery, Jun. 15, 2011, http://www.midasjournal.org/browse/publication/815,http://hdl.handle.net/10380/3286, pp. 1-10).*

(Continued)

*Primary Examiner* — Bao Long T Nguyen
(74) *Attorney, Agent, or Firm* — Venable LLP; Henry J. Daley

(57) ABSTRACT

A combined teleoperative-cooperative controllable robotic system includes a robotic actuator assembly, a control system adapted to communicate with the robotic actuator assembly, and a teleoperation unit adapted to communicate with the control system. The control system is configured to control at least a first portion of the robotic actuator assembly in response to at least one of a force or a torque applied to at least a second portion of the robotic actuator assembly by a first user for cooperative control. The control system is further configured to control at least a third portion of the robotic actuator assembly in response to input by a second user from the teleoperation unit for teleoperative control.

18 Claims, 7 Drawing Sheets

(51) Int. Cl.
*B25J 3/04* (2006.01)
*B25J 9/16* (2006.01)
*A61B 34/30* (2016.01)
*A61B 34/35* (2016.01)
*A61B 34/00* (2016.01)
*A61B 17/00* (2006.01)
*A61B 90/20* (2016.01)

(52) U.S. Cl.
CPC ............... *B25J 3/04* (2013.01); *B25J 9/1689* (2013.01); *B25J 19/04* (2013.01); *A61B 90/20* (2016.02); *A61B 2017/00115* (2013.01)

(58) Field of Classification Search
CPC ........ G05B 19/423; G05B 2219/41114; G05B 2219/36433; G05B 219/39439; G05B 2219/39529; G05B 2219/40599; G05B 2219/36425; G01L 5/162
See application file for complete search history.

(56) References Cited

U.S. PATENT DOCUMENTS

| | | | | |
|---|---|---|---|---|
| 6,191,760 | B1* | 2/2001 | Jun | G09G 5/10 345/20 |
| 6,212,443 | B1* | 4/2001 | Nagata et al. | 700/245 |
| 6,659,939 | B2* | 12/2003 | Moll et al. | 600/102 |
| 6,837,883 | B2* | 1/2005 | Moll et al. | 606/1 |
| 6,928,490 | B1* | 8/2005 | Bucholz | G06F 19/327 340/12.32 |
| 7,865,266 | B2* | 1/2011 | Moll et al. | 700/245 |
| 8,412,379 | B2* | 4/2013 | Gerio et al. | 700/264 |
| 8,494,677 | B2* | 7/2013 | Mizutani | 700/250 |
| 8,506,555 | B2* | 8/2013 | Ruiz Morales | 606/1 |
| 2003/0030397 | A1* | 2/2003 | Simmons | 318/568.11 |
| 2006/0178559 | A1* | 8/2006 | Kumar | G09B 23/28 600/109 |
| 2008/0132913 | A1* | 6/2008 | Brock et al. | 606/130 |
| 2009/0082905 | A1* | 3/2009 | Green | 700/259 |
| 2009/0099520 | A1* | 4/2009 | Millman et al. | 604/131 |
| 2009/0259412 | A1* | 10/2009 | Brogardh | 702/41 |
| 2009/0276105 | A1* | 11/2009 | Lacaze et al. | 701/2 |
| 2010/0013153 | A1* | 1/2010 | Yourlo et al. | 273/237 |
| 2010/0169815 | A1* | 7/2010 | Zhao et al. | 715/771 |
| 2010/0234857 | A1* | 9/2010 | Itkowitz et al. | 606/130 |
| 2010/0250023 | A1* | 9/2010 | Gudat | 701/2 |
| 2010/0256812 | A1* | 10/2010 | Tsusaka et al. | 700/254 |
| 2011/0178638 | A1* | 7/2011 | Tsusaka et al. | 700/257 |
| 2011/0208000 | A1* | 8/2011 | Honda | A61B 1/00016 600/118 |
| 2011/0224689 | A1* | 9/2011 | Larkin et al. | 606/130 |
| 2012/0004791 | A1* | 1/2012 | Buelthoff et al. | 701/2 |

OTHER PUBLICATIONS

Abbott et al., "Pseudo-admittance Bilateral Telemanipulation with Guidance Virtual Fixtures," The International Journal of Robotics Research, 2007, 26(8), 865-884. doi:10.1177/0278364907080425.

Abbott et al., "Stable Forbidden-Region Virtual Fixtures for Bilateral Telemanipulation," Journal of Dynamic Systems, Measurement, and Control, 2006.

Balicki et al., "Micro-force sensing in robot assisted membrane peeling for vitreoretinal surgery," In: Proceedings of MICCAI 2010. Cisst Library http://trac.lcsr.jhu.edu/cisst, May 2013.

Das et al., "Evaluation of a telerobotic system to assist surgeons in microsurgery," Computer Aided Surgery 4(1):15-25. 1999.

Ida et al., "Microsurgical robotic system for vitreoretinal surgery," Int J CARS 2011.

Jung et al., "A Component-based Architecture for Flexible Integration of Robotic Systems," In IEEE/RSJ IROS, pp. 6107-6112, Oct. 18-22, 2010.

Jung et al., "A Surgical Assistant Workstation (SAW) Application for a Teleoperated Surgical Robot System," in MICCAI Workshop on System, 2009.

Kapoor et al., "Constrained Control for Surgical Assistant Robots," In Proceedings of IEEE ICRA, pp. 231-236, 2006.

Khademian et al., "A four-channel multilateral shared control architecture for dual-user teleoperation systems," . . . Systems, 2007. IROS 2007 . . . , 2660-2666. doi:10.1109/IROS.2007.4399225.

Mitchell et al., "Development and application of a new steady-hand manipulator for retinal surgery," In Proceedings of IEEE ICRA, pp. 623-629, 2007.

Moghimi et al., "Haptic-enabled Collaborative Training with Generalized Force and Position Mappings," 2008 Symposium on Haptic Interfaces for Virtual Environment and Teleoperator Systems, 287-294. doi:10.1109/HAPTICS.2008.4479960.

Nudehi et al., "A shared-control approach to haptic interface design for minimally invasive telesurgical training," IEEE Transactions on Control Systems Technology, 13(4), (2005) 588-592. doi:10.1109/TCST.2004.843131.

Uneri et al., "New steady-hand EyeRobot with micro-force sensing for vitreoretinal surgery," In: Proceedings of IEEE BioRob, pp. 814-819, Sep. 26-29, 2010.

Xia et al., "A constrained optimization approach to virtual fixtures for multi-robot collaborative teleoperation," 2011 IEEERSJ International Conference on Intelligent Robots and Systems 639-644 (Sep. 25-30, 2011). IEEE. doi:10.1109/IROS.2011.6048816.

* cited by examiner

Page 1 of 2 (Columns 1-2)

TELEOPERATIVE-COOPERATIVE ROBOTIC SYSTEM

CROSS-REFERENCE OF RELATED APPLICATION

This application claims priority to U.S. Provisional Application No. 61/540,145 filed Sep. 28, 2011, the entire content of which is hereby incorporated by reference.

This invention was made with Government support of Grant No. 1R01 EB 007969-01, awarded by the Department of Health and Human Services, The National Institutes of Health (NIH); and Grant No. EEC-9731478, awarded by the National Science Foundation (NSF). The U.S. Government has certain rights in this invention.

BACKGROUND

1. Field of Invention

The field of the currently claimed embodiments of this invention relates to robotic systems, and more particularly to combined teleoperative-cooperative controllable robotic systems.

2. Discussion of Related Art

Robotic microsurgery has great potential to address common problems encountered in many micromanipulation tasks including hand tremor, poor tool manipulation resolution, and accessibility. Robotic manipulators can provide the needed stability and precision, especially in a task like vitreoretinal eye surgery. Although there are numerous robotic eye surgery concepts, we employ two types of different robotic paradigms to address these problems.

One type is the cooperative control robot, such as the EyeRobot2 (ER2), where the surgeon and robot share the control of the surgical instrument. In this type, the robot holds the surgical tool. The surgeon holds the surgical tool or a handle or sensing device that moves with the robot's tool holder. The robot control system senses forces exerted by the surgeon on the tool or handle and moves the robot in accordance with the sensed forces. In other embodiments, the system may sense handle displacements and move in response to those. The main advantages are that the operator interaction with the surgical instruments is familiar and direct but much steadier than freehand operation and that the surgeon can remove the tool from the eye at any moment, without delay. This is very important in cases where the patient is locally anaesthetized and awake, and can move unexpectedly.

Another type is a teleoperation system where the surgeon controls the robotic manipulator from a remote master console. The best known example of a teleoperation system is the da Vinci Surgical System® (Intuitive Surgical, Inc.), a commercially available and clinically approved telerobotic system for Minimally Invasive Surgical procedures (MIS). This system has similar advantages of minimizing hand tremor, but can provide an even finer degree of tool control by employing a motion scaling scheme. There are a few disadvantages to teleoperation, including difficulty in performing safe gross motion inside and outside of the eye due to lack of visualization, significant reliance on correct definition of the location of the remote-center-of-motion mechanism that prevents excessive motion of the eye by constraining tool motion to intersect the sclerotomy incision location, and the increased slave design complexity to comply with stringent safety requirements. Therefore, there remains a need for improved robotic systems.

SUMMARY

A combined teleoperative-cooperative controllable robotic system according to some embodiments of the current invention includes a robotic actuator assembly, a control system adapted to communicate with the robotic actuator assembly, and a teleoperation unit adapted to communicate with the control system. The control system is configured to control at least a first portion of the robotic actuator assembly in response to at least one of a force or a torque applied to at least a second portion of the robotic actuator assembly by a first user for cooperative control. The control system is further configured to control at least a third portion of the robotic actuator assembly in response to input by a second user from the teleoperation unit for teleoperative control.

BRIEF DESCRIPTION OF THE DRAWINGS

Further objectives and advantages will become apparent from a consideration of the description, drawings, and examples.

DETAILED DESCRIPTION

Figure 1:
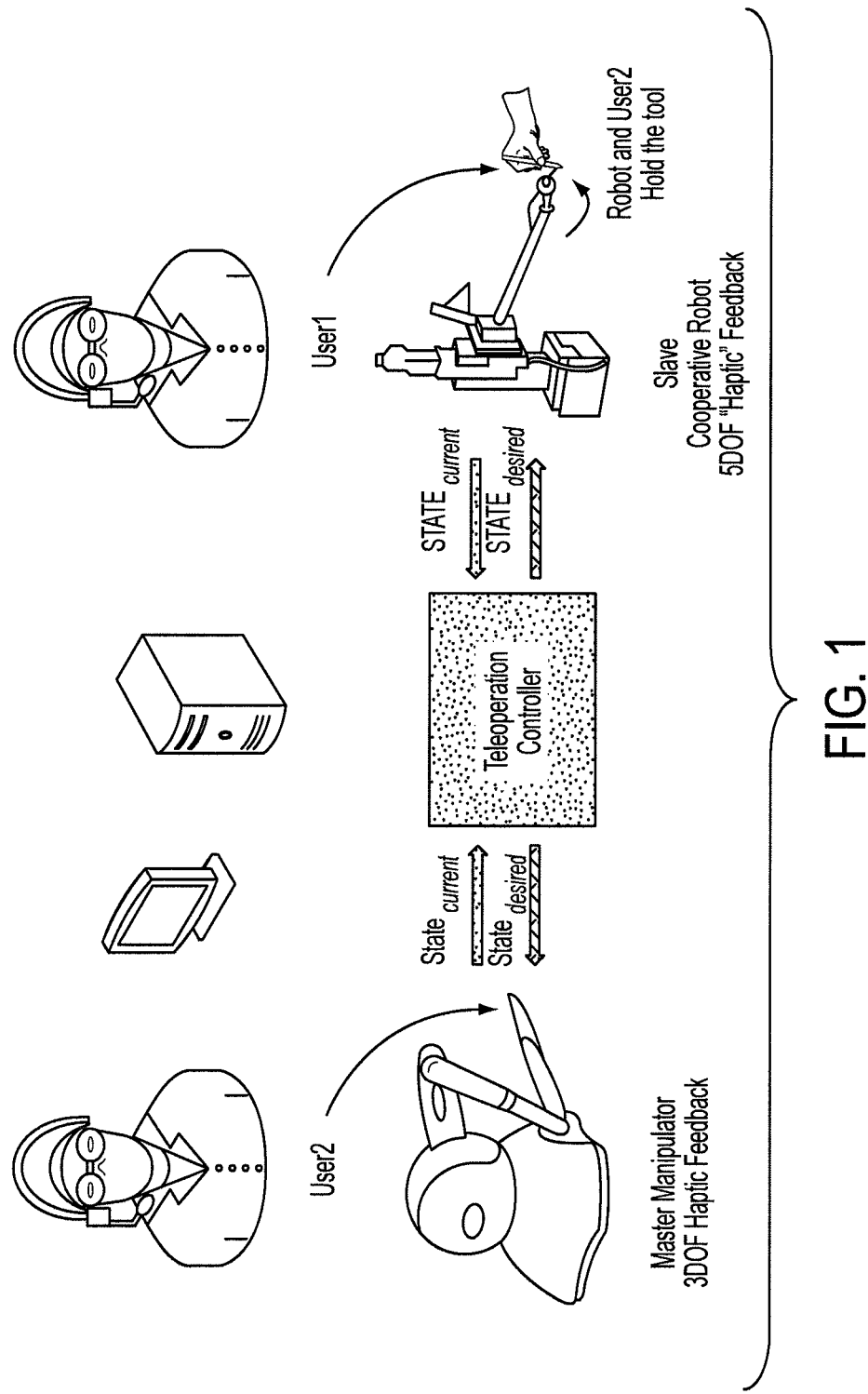
FIG. 1 is a schematic illustration of a combined teleoperative-cooperative robotic system according an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Microsurgical manipulation requires precise manual dexterity, fine visual-motor coordination, and application of forces that are well below human tactile sensation. Imprecise movements during these operations are further attributed to physiological hand tremor, fatigue, poor visual and kinesthetic feedback, as well as patient movement. In vitreoretinal surgery, the common microsurgery risks and limitations are further extended by surgical inaccessibility, poor visibility, tissue fragility and the flexibility of delicate (20-25 Ga) surgical instruments.

Epiretinal membrane peeling is a typical task where a thin membrane is carefully delaminated off the surface of the retina by grasping the membrane's edge with micro-forceps and pulling it free from the retina. Due to unstable manipulation, and unknown forces applied to the tissue, the maneuver is associated with the risks of retinal hemorrhage and tearing, leading to potentially irreversible damage that results in vision loss. Surgeons manipulate the peeling tissue at very slow instrument velocities, observed to be within 0.1-0.5 mm/s range, and simultaneously visually monitor local surface deformation that may indicate undesirable forces between the surgical instrument, the membrane and the retina. A capable surgeon reacts to such cues by retracting the instrument and re-grasping the tissue for an alternate approach. This task is extremely difficult to master due to nearly imperceptible visual cues, and a requirement for very precise visuomotor reflexes. Factors such as involuntary patient motion, inconsistent tissue properties, high or variable tool velocities, and changing manipulation directions can dramatically increase undesirable forces applied to the delicate retinal tissue. Increasing the manipulation precision and instrument stability by incorporating a robot into the surgical task and actively sensing, limiting and presenting these forces to the surgeon have the potential to significantly improve surgical precision and diminish surgical complications.

Both teleoperative control and cooperative control systems are capable in aiding in only specific aspects of the surgical tasks. By combining the functionality of both systems according to embodiments of the current invention, the coverage is much more practical.

The following summarizes some current limitations with conventional standalone systems:

Teleoperation:
Due to safety concerns, translating the eye with a telerobotic instrument is generally slow and considered dangerous without complex sensing elements.
In many cases, gross positioning of the slave manipulator is cumbersome.
Fast tool manipulation is considered dangerous.
It is difficult to detect a surgical emergency from a remote site. Resulting ejection of the tool from the eye may involve unacceptable latency.
Complex control is required to respect eye's physical constraints.

EyeRobot:
User generated micro-motion on order of microns is possible but still difficult.
Only a single operator can manipulate the instrument at a time.

Surgical training is another area where embodiments of the current invention can be beneficial. Typically novice surgeons train by watching experienced surgeons perform the actual surgery. Then they try to do a few simple procedures themselves while the experienced surgeon verbally guides them through it. The verbal communication can be risky, and inefficient. Demonstrations are also impractical due to the time required to switch in and out of operating position. A hands-on type of training where the teacher can take over anytime or adjust the students' technique in real time is highly desirable.

An embodiment of the current invention integrates these two paradigms into a single hybrid telerobotic system to combine the advantages and supplement the weaknesses found in the respective standalone systems while addressing the major challenges of microsurgery.

FIG. 1 provides a schematic illustration of a combined teleoperative-cooperative controllable robotic system 100 according to an embodiment of the current invention. The combined teleoperative-cooperative controllable robotic system 100 includes a robotic actuator assembly 102, a control system 104 adapted to communicate with the robotic actuator assembly 102, and a teleoperation unit 106 adapted to communicate with the control system 104. The control system 104 is configured to control at least a first portion of the robotic actuator assembly 102 in response to at least one of a force or a torque applied to at least a second portion of said robotic actuator assembly by a first user 108 for cooperative control. The control system 104 is further configured to control at least a third portion of the robotic actuator assembly 102 in response to input by a second user 110 from the teleoperation unit 106 for teleoperative control.

The term "cooperative control" is intended to refer to a robotic system in which the user interacts directly with at least a portion of the robotic actuator assembly so that the robot effectively assists the user in performing certain operations. In this case, the user is located in close proximity to the robotic actuator assembly. FIG. 1 shows one possible example in which user 1 (108) grabs a tool that is attached to the robotic actuator assembly 102. The motion of the tool, for example, is then a result of cooperative actions by both the user 108 and the robot.

The term "teleoperative control" is intended to refer to a robotic system in which the user interacts indirectly with at least a portion of the robotic actuator assembly through a physically separated device. In that case, the user is in a separate location from the robotic actuator assembly. In many applications, this can be a distance of a few feet to a few tens of feet, for example, in a different place in the same room. However, greater distances are also possible in some embodiments.

Although FIG. 1 illustrates an embodiment of a combined teleoperative-cooperative controllable robotic system 100 that has one robotic actuator assembly 102 and/or the teleoperation unit 106, the broad concepts of the current invention are not limited to only this example. For example, a second, third or more teleoperation units could be included. Alternatively, or in addition, a second, third, or more robotic actuator assemblies could be included.

The first portion of said robotic actuator assembly 102 can be the same portion of the robotic actuator assembly 102 as the second portion and/or the same portion of said robotic actuator assembly 102 as the second portion. However, in some embodiments, each of the first, second and third portions of the robotic actuator assembly 102 can all be different components.

In FIG. 1, the control system 104 is represented schematically as being localized between the robotic actuator assembly 102 and the teleoperation unit 106. However, the broad concepts of the current invention are not limited to only that particular arrangement. The control system 104 could be a distributed system such that portions are located in the robotic actuator assembly 102 and/or the teleoperation unit 106, for example, in addition to, or instead of, being localized separately. In addition, communication between the robotic actuator assembly 102 and/or the teleoperation unit 106 can be by wire, cable, optical fiber, and/or wirelessly, for example.

In some embodiments, the control system 106 can be configured to control portions of the robotic actuator assembly in response to input from both the first user 108 and the second user 110 with a scaling factor so that input from one of the first and second users (108, 110) is weighted more strongly than input from the other of the first and second users.

In some embodiments, the control system 104 can be configured to control the portion of the robotic actuator assembly 102 based on input from one of the first and second users overriding input from the other of the first and second users.

In some embodiments, the robotic actuator assembly 102 includes a surgical tool such that the combined teleoperative-cooperative robotic system is a surgical robotic system. The surgical tool can be selectively attachable, permanently attached or integral with the robotic actuator assembly 102, for example. The robotic actuator assembly 102 is not limited to only one tool. In some embodiments, there can be two, three or more tools attached.

In some embodiments, the robotic actuator assembly 102 includes an end effector adapted to interact with an object of interest. In further embodiments, the teleoperative-cooperative robotic system can include a sensor arranged to sense a physical property associated with the end effector interacting with the object of interest (not shown in FIG. 1). The sensor can be, but is not limited to, an optical sensor or a force sensor, for example. An optical sensor can include, but is not limited to, an optical coherence tomography (OCT) system, for example. Furthermore, two or more sensors could also be included. The sensor can be adapted to communicate with the control system to provide information regarding the physical property sensed, and the control system can be configured to modify control of the portion of the robotic actuator assembly based on the information from the sensor.

In some embodiments, the control system 104 can be configured to be switchable between cooperative control and teleoperative control such that the first user and said second user can direct different types of tasks. For example, the different types of tasks can include macro control tasks to be performed by the first user and micro control tasks to be performed by the second user. However, this is only an example. Different and more complex classifications of tasks are also within the scope of other embodiments.

In some embodiments, the control system 104 can be configured to provide feedback to the teleoperation unit 106 based on the at least one of the force or the torque applied by the first user 108. The feedback can include, but is not limited to, a haptic feedback, an audible feedback and/or a visual feedback. A haptic feedback can include causing portions of the teleoperation unit 106 to move in correspondence to motions of the robotic actuator assembly 102, for example.

In some embodiments, the combined teleoperative-cooperative robotic system 100 can further include an imaging system (not shown in FIG. 1) arranged in view of an object of interest; and a display system 112 arranged at least one of proximate the teleoperation unit 106 to display images of the object of interest to be viewed by the second user 110, or proximate the robotic actuator assembly 102 to display images of the object of interest to be viewed by the first user 108. The imaging system can include one or more cameras, for example. The display system can include one or more image display devices. Although the image display system 112 is represented schematically as a display screen in that particular example, the invention is not limited to one or more display screens. A display device can be built into the teleoperation unit 106 in a console configuration, for example. However, these are just a few examples that are not intended to limit the broad scope of the invention. In further examples, the imaging system can also include a microscope such that the teleoperative-cooperative robotic system 100 is adapted for performing micromanipulation. The micromanipulation can be, but is not limited to, micro-assembly and/or micro-surgery, for example.

In some embodiments, the display system 112 can adapted to communicate with a data storage system 114 to receive information from the data storage system 114 to be displayed by the display system. The data storage system 114 can be part of a computer system, for example. The computer system can be a localized computer such as a server, a workstation, a desktop computer, a lap top computer, or any other suitable computer and data storage device. It can also be a distributed computer system, such as networked computers, which can include, but are not limited to, computers connected by the internet. The display system 112 and/or data storage system can communicate with the control system 104 through hard-wire and/or wireless connections.

The display system 112 can be configured to display the information from the data storage system 114 at least one of alternately with the images of the object of interest or superimposed with the images of the object of interest. The broad concepts of the current invention are not limited by the types of data that can be stored in data storage system 114 and displayed on display system 112. In the case of robotic surgery, it can often be useful to display preoperative data superimposed over the real-time images, for example. Preoperative data can include, but is not limited to, MRIs, CT scans, OCT scans, etc.

In some embodiments, the robotic actuator assembly 102 and the control system 104 are configured to provide a user input function such that the first user 108 can at least one of control or annotate images on the display system 112. In some embodiments, this can be thought of in analogy of a mouse. Interactions of the user 108 with the robotic actuator assembly 102 can effectively provide an input device for the user 108. Feedback such as audible feedback similar to a mouse click can be included in some embodiments.

The following describes, without limitation, some of the various possible modes of use.

Hybrid Teleoperation Control Swapping—Either Master or Slave can Control the Tool A clutch signal can be used to switch the primary input that completely controls the motion of the tool. For example: User1 is manipulating the tool through cooperative control on slave robot. User2 holds down a button on handle of master manipulator at which point User1 no longer controls the tool. The tool is controlled via User2 through teleoperation.

External computer makes the decision to switch based on information about the procedure:

Example—computer vision detects that a tool has moved in/out of proximity of a target: User1 drives the tool once it is close to a target and relinquishes control to User2.

The clutch signal could be a physical button on the devices, or a virtual button on a GUI.

The clutch signal could also be triggered when user's input force on either device exceeds a threshold. This mode requires feedback to the master.

For example: User2 is manipulating the tool through teleoperation. User1 grasps the tool and attempts to move the robot so that a large force is sensed on the cooperative robot's tool handle force torque sensor causing a switch so that User2 is no longer contributing to the motion of the slave. User1 is not in control until a button is clicked to switch back. Alternatively, if haptic (force) feedback to the master is available, the User2 can take over the control of the tool by exceeding a force application threshold on the master manipulator.

Feedback (bilateral teleoperation) to the master is optional.

In one possible embodiment User1's motion is reflected to User2.

Hybrid Teleoperation Concurrent Control:

The motion of the tool is a combination of User1's and User2's inputs.

This can include haptic feedback on the master manipulator (bilateral teleoperation).

Any virtual fixtures on the slave side are naturally reflected to the master.

Relative contribution from the users can be adjusted to give one of the users control priority.

This mode can be combined with the control swapping methods from above (e.g. switch upon a threshold force).

Sharing does not have to be equally proportional in all the degrees of freedom. i.e. some degrees are controlled by User2 and others are controlled by User1; User2 has more control of up/down, while User1 has more control of left/right.

In addition, various embodiments for the master side are possible:
A digitizer, such as optical tracker, or a CMM arm
3D mouse or a tablet
Haptic feedback device such as a Phantom Omni
A surgical master console such as the DaVinci
Another cooperatively controlled robot
Some additional embodiments can include the following:
The slave can be used as an input into a graphical user interface. i.e. User1 manipulates the slave's handle while it is stopped. The forces are transformed into 2D or 3D motion on the GUI, a function similar to a force joystick. This may be used for telestration using the slave as input.
It can also be used as a selection mechanism for changing operational modes in 1D or 2D. Audio feedback could be used to communicate the current state:
Example—User2 drives the slave robot, User1 twists tool handle—(double click) this is detected triggering event.
Multiple devices can be utilized at either the remote or local end.

Figure 2:
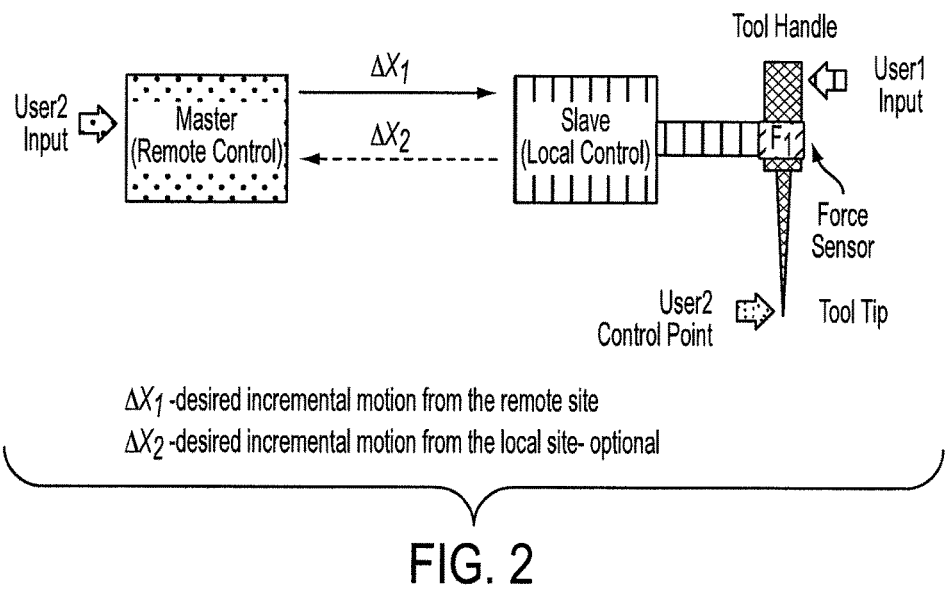
FIG. 2 is a schematic illustration to help explain some concepts of an embodiment of the current invention.
Figure 3:
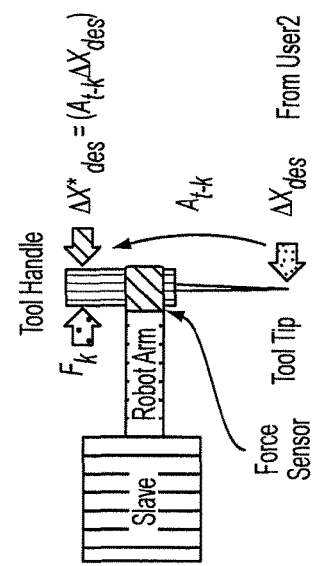
FIG. 3 is a schematic illustration to help explain some concepts of a control scheme according to an embodiment of the current invention.

FIG. 2 provides a schematic illustration that helps explain combined teleoperative-cooperative control according to an embodiment of the current invention. FIG. 3 illustrates a particular control scheme according to an embodiment of the current invention.

The followings examples describe some embodiments in more detail. The broad concepts of the current invention are not intended to be limited to the particular examples.

EXAMPLES

Figure 4:
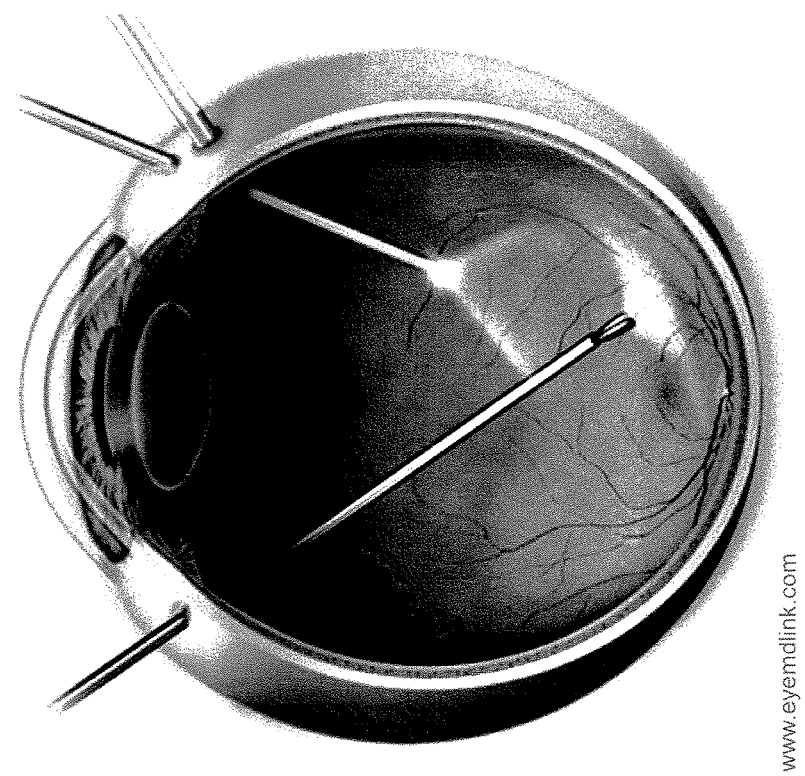
FIG. 4 shows a surgeon operating (left), and a schematic illustration of forceps and light pipe instrument inside the eye during a surgical procedure.
Figure 4:
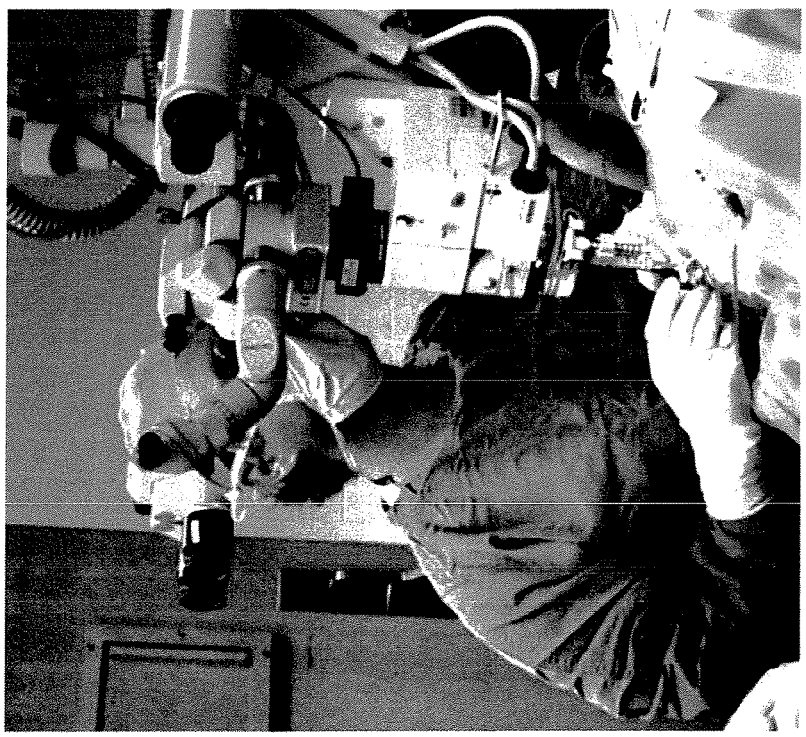

Vitreo-retinal surgery is the most technically demanding ophthalmologic discipline. It addresses common sight-threatening conditions including retinal detachment, complications from diabetes, macular pucker, macular hole and removal of retina-associated scar tissue [1]. In current practice, retinal surgery is performed under an operating stereo-microscope with free-hand 20-25 gage instrumentation. In most cases, three incisions in the sclera (sclerotomy) are required: one for infusion to control the intra-ocular pressure, one for a fiber-optic "light pipe" and one for a surgical instrument (see FIG. 4). The surgeons often operate in bimanual fashion with a "light pipe" in one hand and a forceps, laser, vitreous-cutting probe, fragmenter, aspiration, or another type of tool in the other hand. A typical vitro-retinal surgical task is peeling epiretinal membranes from the surface of the delicate retina. Another task which is considered too difficult, but very desirable, is cannulating 100 µm diameter retinal vessels for targeted drug delivery. Surgeons strive to overcome many human and technological limitations that include physiological hand tremor, poor visualization of surgical targets, and lack of tactile feedback in tool-to-tissue interactions.

In this example according to an embodiment of the current invention, we address these challenges in a systems-based approach, creating the Eye Surgical Assistant Workstation (eyeSAW) platform for development and testing of micro-surgical robots, intra-operative sensors, human-machine interaction, robot control methods and new surgical procedures with vitreo-retinal surgery as the driving application.

Robotic manipulators are inherent parts of the system and can provide the needed stability and precision. Although there are numerous robotic eye surgery concepts, we used two for this example. One type is the cooperative control robot, such as the EyeRobot2 (ER2), where the surgeon and robot share the control of the surgical instrument [2]. The main advantages are that the operator interaction with the surgical instruments is familiar and direct but much steadier than freehand operation and that the surgeon can remove the tool from the eye at any moment, without delay. This is very important in cases where the patient is locally anaesthetized and awake, and can move unexpectedly.

Another type is a tele-operation system where the surgeon controls the robotic manipulator from a remote master console [3], the best known example is the da Vinci Surgical System® (Intuitive Surgical, Inc.), a commercially available and clinically approved tele-robotic system for Minimally Invasive Surgical procedures (MIS). This system has similar advantages of minimizing hand tremor, but can provide an even finer degree of tool control by employing a motion scaling scheme. There are a few disadvantages, including difficulty in performing safe gross motion outside of the eye due to lack of visualization, significant reliance on correct definition of the location of the remote-center-of-motion mechanism that prevents excessive motion of the eye by constraining tool motion to intersect the sclerotomy incision location, and the increased slave design complexity to comply with stringent safety requirements.

Figure 5:
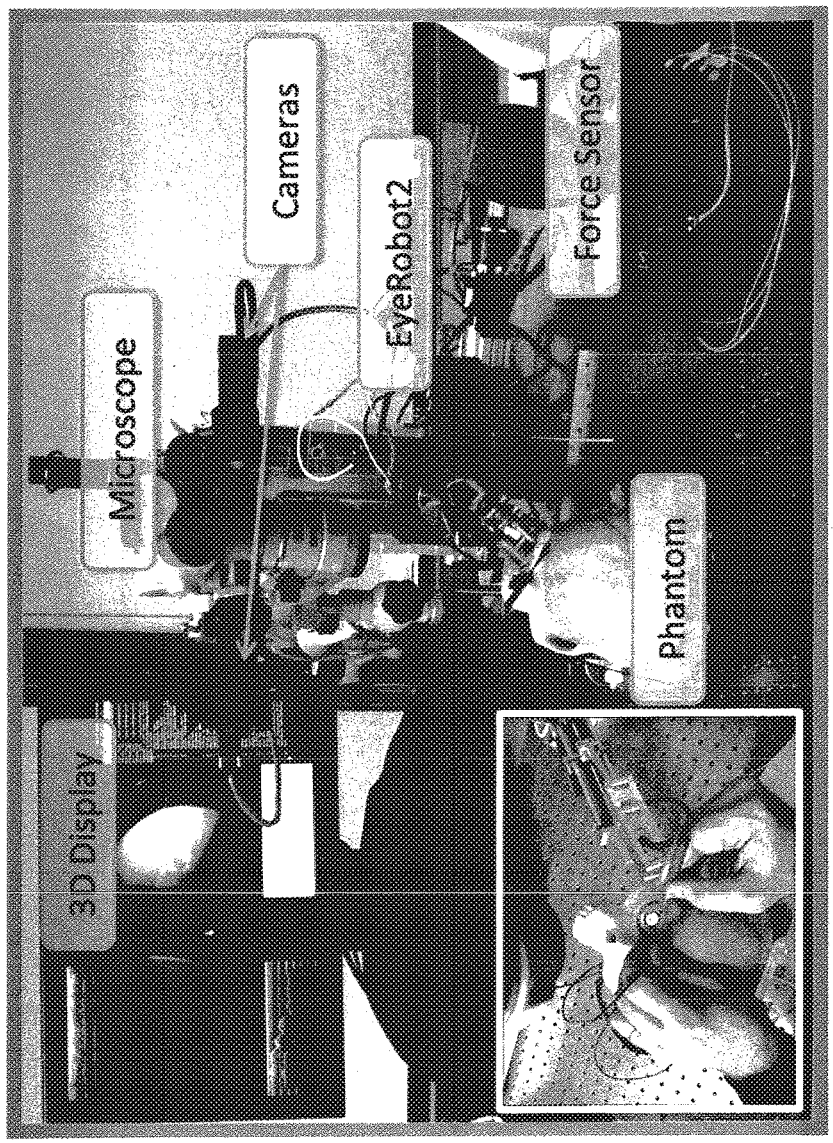
FIG. 5 shows a teleoperative-cooperative robotic system according an embodiment of the current invention using slave side display with EyeRobot2 and a daVinci Master Console.

We believe that incorporating these two paradigms into a single hybrid tele-robotic and cooperative system can combine the advantages and supplement the weaknesses found in the respective standalone systems. In this example, we present a prototype of such a tele-robotic surgical system, including overall architecture, EyeRobot2 and daVinci Master manipulators, and visualization, and various user interaction modes that incorporate teleoperation, cooperative control, and real time sensing information (see FIG. 5).

System Architecture

The eyeSAW relies heavily on the concept of component based system design by which new surgical system configuration and functionality can be rapidly prototyped with minimal or no modifications to existing devices and applications. The cisstMultiTask (MTS) library provides this underlying component-based software framework [9]. It supports two different architectures, a multi-threaded architecture that has optimal performance for robot control applications and a multi-process or distributed architecture that is scalable and extensible. The same programming model [4] allows these two architectures to be seamlessly and flexibly combined together to build a system with minimal source code changes at the user level. The connection and coordination of components in a system is managed by the Global Component Manager (GCM), which is unique to the system and defines the system boundary.

Figure 6:
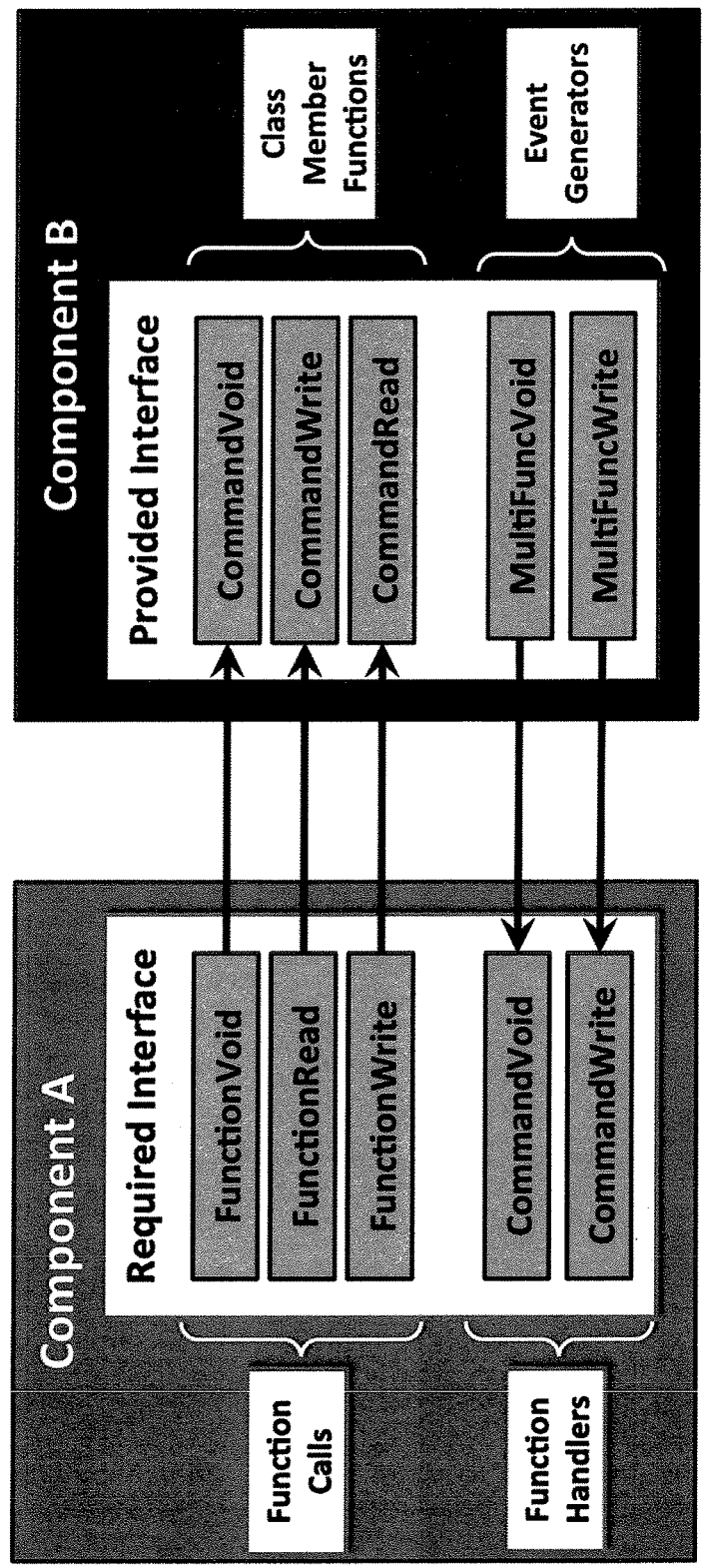
FIG. 6 is a schematic of component interface connections according to an embodiment of the current invention.

The basic building block is a software component which has a list of standard commands contained in provided and required interfaces. The component (A) that needs specific functionality has a required interface that is connected to another component (B)'s provided interface, which provides that functionality (see FIG. 6). Upon connection, a component A can initiate a command, which executes B's function or receives an event command from B. One advantage is that B can be replaced by another component/device (C) that supplies a matching provided interface required by A. When the components are in the same process, the command execution is comparable to a standard function call. In the case when the components are distributed over a network, a typical round trip execution of a command over a multi-hop network with a payload of 150 bytes is 300 µs, which, for most applications, is an acceptable execution time.

Figure 7:
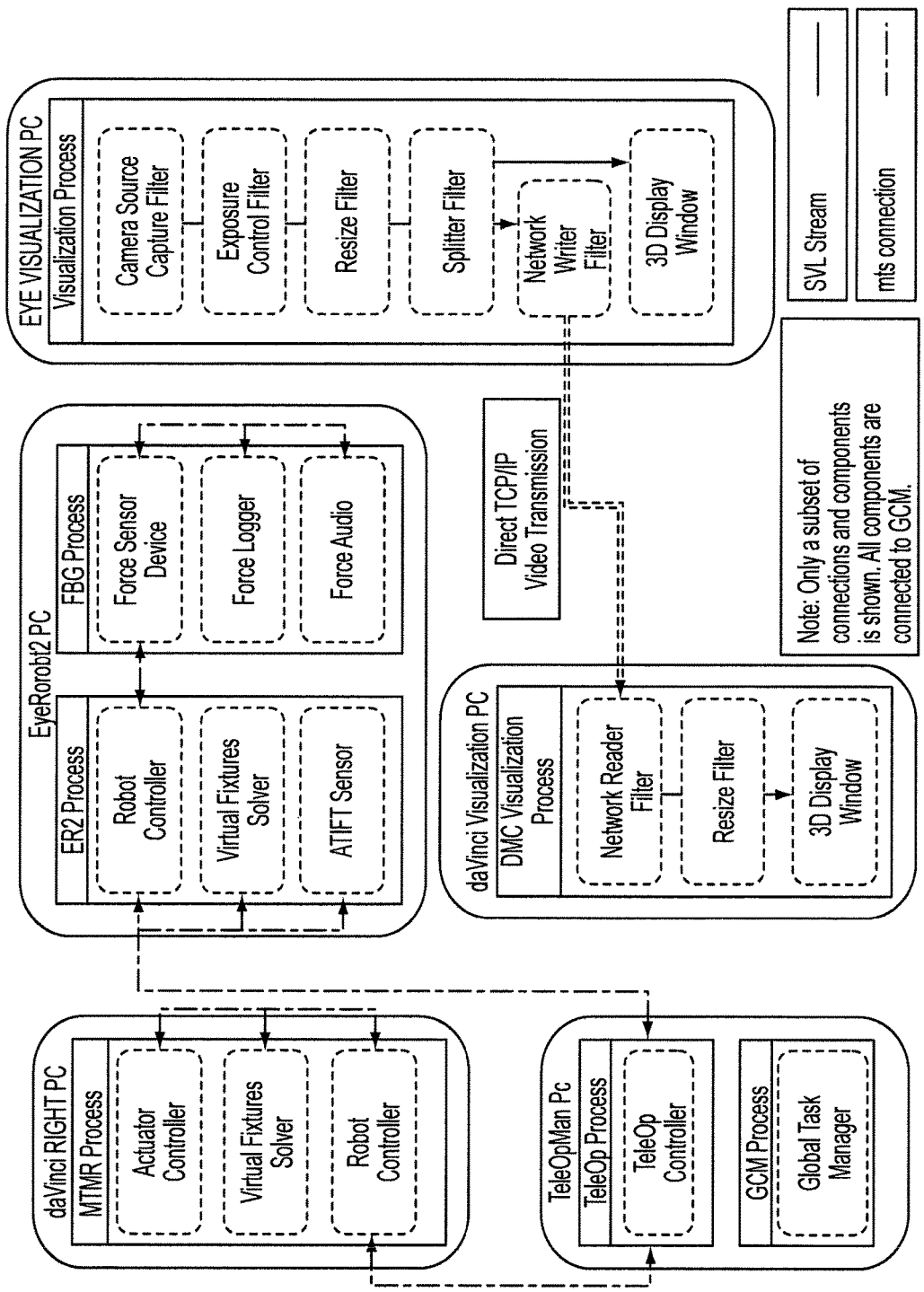
FIG. 7 is the eyeSAW hardware/software view schematic with connections according to an embodiment of the current invention.

Using the above framework, we have created a master/slave tele-robotic surgical system according to an embodiment of the current invention that uses existing devices and their component software interfaces (see FIG. 7). A new component was added, serving as a bridge between the two robotic manipulators and executing tele-operation algorithms. To facilitate tele-visualization we have built a custom stereo video encoding and display subsystem.

da Vinci Master Console (DMC)

Through a collaboration agreement with Intuitive Surgical Inc., we have acquired the mechanical subsystem, which includes two Patient Side Manipulators (PSM) and a daVinci Master Console (DMC) unit, comprising two Master Tele-Manipulators (MTM) and stereoscopic display system. Each MTM is a cable driven 7-DoF serial robot with a redundant wrist mechanism. Our custom system, using custom electronics and software, allows for low-level joint level control, enabling haptic force feedback research, which is not available on the commercial system.

We want to use intra-operative sensing, from OCT or force sensors, to generate virtual fixture (VF) motion constraints that help the surgeon to perform a task. Virtual fixtures are task-dependent motion constraints for a robotic manipulator performing a task by limiting its movement into a restricted workspace and/or influencing its motion along a desired path and are classified as Forbidden Region (FRVF) or Guidance (GVF) virtual fixtures, respectively. VF primitives such as stay above a plane, move along a line, and rotate about a point can be combined using different operators to provide assistance for complex surgical tasks. We implement VFs using the constrained optimization formulation below, where $C(X(q+\Delta q), X_d)$ is the objective function associated with the difference between the actual state variable X and the desired state variable $X_d$. The state, $X=X(q+\Delta q)$ is a function of joint variables q and joint incremental motion $\Delta q$. The solution vector $\Delta q_c$ must satisfy motion constraints in the form of one or more inequalities $A(X(q+\Delta q)) \leq b$. In addition, we make use of constraints that involve $\Delta q_U$ and $\Delta q_L$, the upper and lower rate limit for $\Delta q$. For each control step, the optimization controller computes a desired incremental motion $\Delta q_c$, based on constraints and objectives generated from various real-time input sources [5].

$$\Delta q_c = \min C(X(q+\Delta q), X_d)$$

$$s.t.\ A(X(q+\Delta q)) \leq b, \Delta q_L \leq \Delta q \leq \Delta q_U$$

We also implement bilateral feedback. When the slave encounters a force in the environment, (e.g., obstacle), it lags behind the command position and the user haptically feels this resistance, as the bilateral feedback objective acts to minimize the daVinci master and EyeRobot2 tracking error, by opposing the user's input motion on the daVinci master.

EyeRobot2 (ER2)

The Eye Robot2 is a cooperatively-controlled robot assistant designed for retinal microsurgery. In cooperative control, the surgeon and the robot both hold and control the surgical instrument simultaneously. The ER2 can assist during high-risk procedures, by incorporating virtual fixtures to help protect the patient, and by eliminating physiological tremor in the surgeon's hand during surgery. It is a 5-DOF serial manipulator with XYZ stages for the base and two rotary stages that create a mechanical Remote Center of Motion (RCM). The user "drives" the robot by manipulating the tool which is attached to a 6-DOF force sensor. Like the MTM above, the control software is based on the cisst library, complies with the SAW framework, and uses the Constrained Control Optimization library to calculate incremental joint motions. Its high level control loop runs at 250 Hz and commands the motion controller running at 1 kHz (Galil DMC1886 PCI). We have also designed a line of robot-compatible smart surgical instruments that have embedded micro-sensors. These provide direct real-time feedback to the robot which uses this information, if needed, to affect the surgeon's movements to prevent undesirable collisions with the retina, limit forces applied to the delicate tissues, or intuitively guide the surgeon to a particular target in the eye.

Visualization

Currently, video is the sole feedback modality for the surgeons operating inside the eye. In creating a tele-robotic setup we required a video stereo-microscope system with low latency, high frame rate, high resolution, high dynamic range, and Ethernet based communication for long range telecasts. Therefore, we have developed a high performance visualization sub-system built using the cisstStereoVision library (SVL). SVL provides a wide array of highly optimized filters, such as capture device interfaces, image processing, network transmission functionality, overlays and video formatting for stereo-specific displays. The library is highly multi-threaded, adopting the GPU streams concept, where each filter in the pipeline has access to a pool of threads to process the latest video frame. Configuring these filters in a pipeline is simple, allowing for rapid prototyping of various display architectures, e.g. tele-operation. FIG. 7 shows the two display applications linked by a TCP/IP connection.

The slave system's visualization comprises a standard ophthalmological surgery stereo-microscope (Zeiss OPMI-MD) outfitted with two IEEE-1394B capture cameras (Grasshopper by Point Grey Research) each capturing 1024×768 pixels resolution images at 45 FPS. The left and right video streams are interlaced and rendered on a passive 3D display (PSP2400 by Panorama Technologies) which separates left/right lines using passive polarized glasses. The capture and display latency is a few frames, on a modern multi-core Linux OS workstation. The stereo video stream is also split, encoded with lossy jpeg compression, and sent using NetworkWriter Filter over TCP/IP to the master's display subsystem. Intraframe encoding was chosen to minimize latency. In our prototype system we used a switched gigabit Ethernet network to transfer the dual XGA progressive video stream with a fairly low, approximately 6% (16×) average compression ratio in order to keep the quality loss introduced by the compression close to the source image SNR. The resulting video bandwidth was around 56 Mbps. Encoding latency is under 20 ms thanks to the custom multi-threaded codec implementation.

The master's visualization application running on an older multi-core windows XP machine, uses a very similar SVL pipeline but the video source is provided by the NetworkReaderFilter. This video stream is formatted for DMC's two display CRTs, at 1024×768 pixels per video channel. The display console itself is very ergonomic allowing the optimal alignment of visual and motor axes and offering excellent stereopsis. The final display frame rate is about 25 FPS, with barely noticeable delay of approximately 4-5 frames.

Tele-Operation Manager (TOM)

The TOM is a central component responsible for configuring, monitoring the state, and high-level control of the master and slave components. It also performs position offset computation and clutching. A typical TOM control loop queries the robotic manipulators for their latest Cartesian pose via standard MTS interfaces (e.g., GetFrame (mtsFrm4×4) command), computes the next desired pose and executes a command that sets the goal Cartesian pose on the robotic manipulators (e.g. SetGoalFrame(mtsFrm4×4)). The robots run their own high frequency control loops that servo the robot to the desired pose. The TOM also provides a Qt based GUI that allows the operator to change the tele-operation method, and the workspace motion scaling between the daVinci Master and the Eye Robot.

Control Schemes and Applications

The flexibility and inherent functionality allowed us to quickly prototype a variety of control schemes that extend the functionality of the system beyond the sum of its parts. The two robots and TOM, utilize the robot control constrained optimization framework to calculate incremental joint motion based on system state and given task constraints, e.g. force sensor information. Here are a number of control schemes we have implemented.

Classic unilateral tele-operation (UTO), currently used by the daVinci system, does not include force feedback and the operator is required to close the control loop via the visualization system. This method is sufficient for simple tasks but it lacks fidelity for more complex maneuvers or when visualization is poor and the operating environment does not allow the slave to follow the master, resulting in tracking error.

To diminish the effects of inherent human hand tremor and enable more precise maneuvers found in micro-surgery, motion scaling (MS) was implemented. MS in a tele-operation system involves scaling the Cartesian position of the master by a factor relative to the Cartesian position of the slave.

In bilateral tele-operation (BTO) control the behavior of the slave is fed back into the master controller, and vice versa. If the slave motion is impeded by the environment, the motion of the master manipulator will also be impeded, pragmatically creating a sense of force-feedback. In order to affect the motion of the surgical instrument, the input from both master and slave robot users has to be considered. The slave side controller considers the desired incremental motion ($\Delta X_{des}$) from the BTO as a desired incremental motion of the slave's tool tip. This $\Delta X_{des}$ is transformed into the handle coordinates where it is combined with user desired incremental motion ($\Delta X_h$). The relative importance of the two users can be adjusted by assigning different weights to the two inputs. These inputs can also be capped differently so that one of the users can always overcome the other in controlling the slave's tool. (For example, see FIG. 3.) It is important to note that the EyeRobot2 has only 5 DOF of control, so even though the tele-operation algorithm is commanding 6 DOF Cartesian position and orientation, the desired rotation about the tool axis is omitted by the ER2 control optimizer.

The BTO control scheme is compatible with virtual fixtures (VF) [6] such as the virtual RCM (vRCM) where the tool motion is constrained so the tool shaft always intersects a single point in the robot workspace, e.g. the trocar inside the sclera [7]. The vRCM is implemented on the slave side and inherently reflected back to the master controller via the BTO logic. Since vRCM constrains the motion of the tool to 3 DOF there are a few ways to operate the master side. One way is to implement standard BTO on the master side, and another is to only consider the Cartesian translation of the master (operator is free to rotate the master joystick without affecting the slave) to drive the Cartesian position of the tool tip within the eye.

We have also created dynamic virtual fixtures on the slave manipulator by incorporating real time information from sensors embedded in surgical instruments [8]. One example is micro-force sensing, where interaction forces measured at the tool tip are virtually scaled up through cooperative control. Since the BTO involves position-position exchange the operator on the master side will experience this scaled force reflection.

The intuitive "hand-over-hand" control interface of the EyeRobot2 is very effective in general setup tasks such as gross positioning of the tool near the surgical site, aligning it for insertion through the sclerotomy trocar, or adjusting the position of the vRCM relative to the eye. These tasks are especially difficult in case of pure tele-operation due to lack of macro-field visualization from the microscope. In our system, a technician can quickly position the robot to the desired site, and the surgeon can "clutch-in" with the master and, at any time, take over control with BTO. The BTO can provide very fine positioning for a specific task, especially when used with motion scaling. Furthermore, we have developed a controller located on the slave side that considers both the master's desired motion through BTO, as well as the desired motion of the ER2 operator. This hybrid teleo-operation and cooperative control (HTCC) enables both operators to contribute to the control of the slave manipulator, while complying with any motion constraints, such as vRCM. Depending on the task, it may be more advantageous to have one operator use hands-on control of the slave to prepare for a maneuver and seamlessly "transfer" the control to an operator on the master side to perform the delicate maneuver with finer motion-scaled manipulation. Further, the level of contribution from the two inputs does not have to be equal. By adjusting the relative gains, one of the operators can be the dominant operator. Such control scheme could become a valuable educational tool, where the trainer directly guides the trainee through common surgical tasks.

CONCLUSIONS AND DISCUSSION

The process of developing this tele-operation system has shown that component based software architecture is very convenient for multi-device system prototyping and development. The resulting system is functional and can easily be adopted to accept new devices or to fit other applications, such as micro-vascular surgery, or neuro-surgery. For example, the daVinci master can be replaced with the Phantom Omni (SensAble Technologies Inc) to control EyeRobot2's tool tip while inside the eye with haptic feedback of the 3 DOF. Similarly, we can also add another EyeRobot and the other master manipulator to construct a bi-manual tele-operation system.

The actual process of development with cisstMultiTask was very smooth. Occasionally, additional component interfaces needed to be built, or existing ones extended. The debugging and testing of new modes of operation was efficient due to the ability to disconnect and reconnect specific components/processes without restarting every process in the system.

Despite the slight latency, the tele-visualization system has sufficient frame rate for development purposes. Since our video capture application can handle 1600×1200 px resolution, the system is compatible with newer daVinci master consoles containing higher resolution displays, with little or no compromise in performance. When the master and slave are separated by great distances, the performance will be limited by the large network bandwidth requirement for the JPEG-based intraframe video encoding. For these cases we are considering changing the video encoder to achieve a higher compression ratio and adopting UDP for lower latency. Long distance tele-operation will also require the transmission of audio.

Since EyeRobot2 was designed for pure cooperative control it does not have an actuated tool rotation axis or the ability to open/close instruments on its own. As is, it can be used with axisymmetric instruments such as a surgical pick or illumination guide; for use with more sophisticated tools it can be upgraded with a new tool actuation mechanism that can allow for tele-operation of all available degrees of freedom of the surgical instrument.

The operator of the master console indirectly experiences the dynamic virtual fixtures located remotely on the slave manipulator through standard bilateral tele-operation feedback. In order to provide a higher fidelity feedback for the master console operator, the master can create virtual fixtures locally using real time sensor information collected by the slave system.

The introduction of robots into the surgical flow generally adds to the operation time, yet this disadvantage can be outweighed by the benefits that they provide. From a practical point of view, hybrid tele-operation and cooperative control can overcome a problem when the conventional tele-robotic concept is applied to eye surgery: patient motion. This is especially problematic since the patient is awake and locally anesthetized for most operations. For example, the operator of the EyeRobot2 can assess patient state and anticipate patient motion, e.g., a sneeze.

The ultimate goal of the eyeSAW project is to enable more surgeons to perform currently impossible treatments and improve the safety and success rates of existing vitreoretinal procedures.

REFERENCES

[1] Ida Y. et al. *Microsurgical robotic system for vitreoretinal surgery.* Int J CARS 2011
[2] Uneri A. et al. *New steady-hand EyeRobot with micro force sensing for vitreoretinal surgery.* In: Proceedings of IEEE BioRob, pp 814-819, 2010.
[3] Das H. et al. *Evaluation of a telerobotic system to assist surgeons in microsurgery.* Computer Aided Surgery 4(1): 15-25. 1999
[4] Jung M Y et al. "A Component-based Architecture for Flexible Integration of Robotic Systems," In IEEE/RSJ IROS, pp. 6107-6112, 2010
[5] A. Kapoor, M. Li, and R. H. Taylor. *Constrained Control for Surgical Assistant Robots.* In Proceedings of IEEE ICRA, pp. 231-236, 2006.
[6] Abbott J J. et al. Stable Forbidden-Region Virtual Fixtures for Bilateral Telemanipulation. Journal of Dynamic Systems, Measurement, and Control, 2006.
[7] Mitchell B et al. *Development and application of a new steady-hand manipulator for retinal surgery.* In Proceedings of IEEE ICRA, pp 623-629, 2007.
[8] Balicki M A. et al. Micro-force sensing in robot assisted membrane peeling for vitreoretinal surgery. In: Proceedings of MICCAI 2010.
[9] cisst Library http://trac.lcsr.jhu.edu/cisst
[10] Jung M Y et al. "A Surgical Assistant Workstation (SAW) Application for a Teleoperated Surgical Robot System," in MICCAI Workshop on Systems and Architecture for Computer Assisted Interventions, Midas Journal. 2009

FURTHER REFERENCES

Abbott, J. J., & Okamura, a. M. (2007). Pseudo-admittance Bilateral Telemanipulation with Guidance Virtual Fixtures. The International Journal of Robotics Research, 26(8), 865-884. doi:10.1177/0278364907080425
  Uses impedance as master and simulates admittance type slave with another impedance device. Implements VF on the master only, the desired position is the set point on the slave. No mention of two users, but like most papers it describes the slave interacting with the environment.
Xia, T., Kapoor, A., Kazanzides, P., & Taylor, R. A constrained optimization approach to virtual fixtures for multi-robot collaborative teleoperation, 2011 IEEERSJ International Conference on Intelligent Robots and Systems 639-644 (2011). IEEE. doi:10.1109/IROS.2011.6048816
  Example of virtual fixtures for a surgical knot tying task using a telerobotic system.
Khademian, B., & Hashtrudi-Zaad, K. (2007). A four-channel multilateral shared control architecture for dual-user teleoperation systems . . . Systems, 2007. IROS 2007 . . . , 2660-2666. doi:10.1109/IROS.2007.4399225
  Example of two users operating a master each and sharing the control of a slave. Shows how relative input can be adjusted.
Moghimi, S., Sirouspour, S., & Malysz, P. (2008). Haptic-enabled Collaborative Training with Generalized Force and Position Mappings. 2008 Symposium on Haptic Interfaces for Virtual Environment and Teleoperator Systems, 287-294. doi:10.1109/HAPTICS.2008.4479960
  Example of collaborative training in a virtual environment.
Nudehi, S. S., Mukherjee, R., & Ghodoussi, M. (2005). A shared-control approach to haptic interface design for minimally invasive telesurgical training. IEEE Transactions on Control Systems Technology, 13(4), 588-592. doi:10.1109/TCST.2004.843131
  Example of collaborative (shared control) surgical training with two masters (one per user) and a remote slave.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A combined teleoperative-cooperative controllable robotic system, comprising:
   a robotic actuator assembly including a first robotic manipulator and a second robotic manipulator, wherein said first robotic manipulator differs from said second robotic manipulator;
   a control system adapted to communicate with said robotic actuator assembly; and
   a teleoperation unit adapted to communicate with said control system,
   wherein said control system is configured to control motion of at least said first robotic manipulator of said robotic actuator assembly in response to at least one of a force or a torque applied to at least a portion of said robotic actuator assembly by a first user for cooperative control, wherein said motion of at least said first robotic manipulator of said robotic actuator assembly is a result of cooperative actions by both the first user and the robotic actuator assembly, and
   wherein said control system is further configured to control, concurrently with a motion of said first robotic manipulator, at least said second robotic manipulator of said robotic actuator assembly in response to input by a second user from said teleoperation unit for teleoperative control,
   wherein said control system is configured to control said first robotic manipulator of said robotic actuator assembly in response to input from both said first user and said second user with a scaling factor so that input from one of said first and second users is weighted more strongly than input from the other of said first and second users while preserving concurrent control over said first robotic manipulator by both said first user and said second user in all degrees of freedom available to said first robotic manipulator, and
   wherein said control system is further configured to enable one of said first and second users to control motions of said first robotic manipulator in only selected first degrees of freedom available to said first robotic manipulator and enable the other of said first and second users to control motions of said first robotic manipulator in other selected degrees of freedom available to said first robotic manipulator.

2. A combined teleoperative-cooperative robotic system according to claim 1, wherein said first robotic manipulator of said robotic actuator assembly is the same element of said robotic actuator assembly as said portion.

3. A combined teleoperative-cooperative robotic system according to claim 1, wherein said control system is configured to control said first robotic manipulator of said robotic actuator assembly based on input from one of said first and second users overriding input from the other of said first and second users.

4. A combined teleoperative-cooperative robotic system according to claim 1, wherein said robotic actuator assembly comprises a surgical tool such that said combined teleoperative-cooperative robotic system is a surgical robotic system.

5. A combined teleoperative-cooperative robotic system according to claim 1, wherein said robotic actuator assembly comprises an end effector adapted to interact with an object of interest.

6. A combined teleoperative-cooperative robotic system according to claim 5, further comprising a sensor arranged to sense a physical property associated with said end effector interacting with said object of interest,
   wherein said sensor is adapted to communicate with said control system to provide information regarding said physical property sensed, and
   wherein said control system is configured to modify control of said portion of said robotic actuator assembly based on said information from said sensor.

7. A combined teleoperative-cooperative robotic system according to claim 1, wherein said control system is configured to be switchable between said cooperative control and said teleoperative control such that said first user and said second user can direct different types of tasks.

8. A combined teleoperative-cooperative robotic system according to claim 7, wherein said different types of tasks include macro control tasks to be performed by said first user and micro control tasks to be performed by said second user.

9. A combined teleoperative-cooperative robotic system according to claim 1, wherein said control system is configured to provide feedback to said teleoperation unit based on said at least one of said force or said torque applied by said first user.

10. A combined teleoperative-cooperative robotic system according to claim 9, wherein said feedback comprises at least a haptic feedback causing portions of the teleoperation unit to move in correspondence to motions of said first robotic manipulator.

11. A combined teleoperative-cooperative robotic system according to claim 1, further comprising:
   an imaging system arranged in view of an object of interest; and
   a display system arranged at least one of proximate said teleoperation unit to display images of said object of interest to be viewed by said second user or proximate said robotic actuator assembly to display images of said object of interest to be viewed by said first user.

12. A combined teleoperative-cooperative robotic system according to claim 11, wherein said imaging system comprises a microscope such that said teleoperative-cooperative robotic system is adapted for performing micromanipulation.

13. A combined teleoperative-cooperative robotic system according to claim 12, wherein said micromanipulation is micro-assembly.

14. A combined teleoperative-cooperative robotic system according to claim 12, wherein said micromanipulation is micro-surgery.

15. A combined teleoperative-cooperative robotic system according to claim 11, wherein said display system is adapted to communicate with a data storage system to receive information from said data storage system to be displayed by said display system.

16. A combined teleoperative-cooperative robotic system according to claim 15, wherein said display system is configured to display said information from said data storage system at least one of alternately with said images of said object of interest or superimposed with said images of said object of interest.

17. A combined teleoperative-cooperative robotic system according to claim 16, wherein said robotic actuator assembly and said control system are configured to provide a user input function such that said first user can at least one of control or annotate images on said display system.

18. A combined teleoperative-cooperative robotic system, comprising:
- a robotic actuator assembly including a first robotic manipulator and a second robotic manipulator, wherein said first robotic manipulator differs from said second robotic manipulator;
- a control system adapted to communicate with said robotic actuator assembly;
- a teleoperation unit adapted to communicate with said control system;
- an imaging system arranged in view of an object of interest; and
- a display system arranged at least one of proximate said teleoperation unit to display images of said object of interest to be viewed by said second user or proximate said robotic actuator assembly to display images of said object of interest to be viewed by said first user, wherein said control system is configured to control motion of at least said first robotic manipulator of said robotic actuator assembly in response to at least one of a force or a torque applied to at least a portion of said robotic actuator assembly by a first user for cooperative control, wherein said motion of at least said first robotic manipulator of said robotic actuator assembly is a result of cooperative actions by both the first user and the robotic actuator assembly, wherein said control system is further configured to control, concurrently with a motion of said first robotic manipulator, at least said second robotic manipulator of said robotic actuator assembly in response to input by a second user from said teleoperation unit for teleoperative control, wherein said display system is adapted to communicate with a data storage system to receive information from said data storage system to be displayed by said display system, wherein said display system is configured to display said information from said data storage system at least one of alternately with said images of said object of interest or superimposed with said images of said object of interest, wherein said robotic actuator assembly and said control system are configured to provide a user input function such that said first user can at least one of control or annotate images on said display system, and wherein said robotic actuator assembly and said control system are configured to provide haptic feedback to said first user during said user input function.

* * * * *